Oct. 13, 1942. F. W. ANDERSON Plant Pat. 549

NECTARINE

Filed Oct. 13, 1941

INVENTOR

F. W. Anderson

BY

Webster & Webster

ATTYS

Patented Oct. 13, 1942

Plant Pat. 549

UNITED STATES PATENT OFFICE

549

NECTARINE

Frederic W. Anderson, Merced, Calif.

Application October 13, 1941, Serial No. 414,827

1 Claim. (Cl. 47—62)

This invention relates in general to a new and distinct variety of nectarine, and in particular to a nectarine tree characterized by fruit which has a yellow flesh and a cling stone.

As ordinary commercial varieties of nectarines have notoriously poor shipping qualities, the shipping of these varieties for sale in remote markets has not been practical. In contradistinction the present variety provides a table or dessert type nectarine which, in addition to being juicy and highly edible, is of extremely large size, firm in flesh, and has an excellent shipping quality, being capable of transportation to remote markets without loss of its desirable eating qualities.

The present variety was originated by me on my ranch at Merced, California, as a second generation cross between J. H. Hale peach by Quetta nectarine. Blossoms of the J. H. Hale peach were fertilized with pollen of the Quetta nectarine. Seeds resulting from this cross were planted, and resulted in trees which all produced white-fleshed peaches. Open pollinated seeds of these white-fleshed peaches were planted and the resulting trees brought into bearing. While a majority of such resulting trees were peaches, a substantial number were nectarines, most of the latter being white-fleshed but a few having yellow flesh. One of these yellow-fleshed nectarines was particularly outstanding in its size, appearance and firmness when ripe; this nectarine being the one herein described and claimed.

This particular variety fruited first in 1937 and thereafter was asexually propagated by top working on other trees and nursery seedlings; the trees of the new variety thus asexually propagated now being in bearing and maintaining in full the novel characteristics of the original tree and its fruit.

Figure 1:
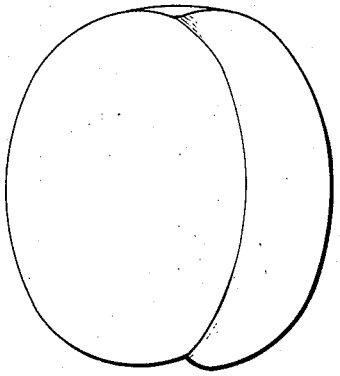
Figure 1 is an outline showing generally the configuration of the fruit.
Figure 3:
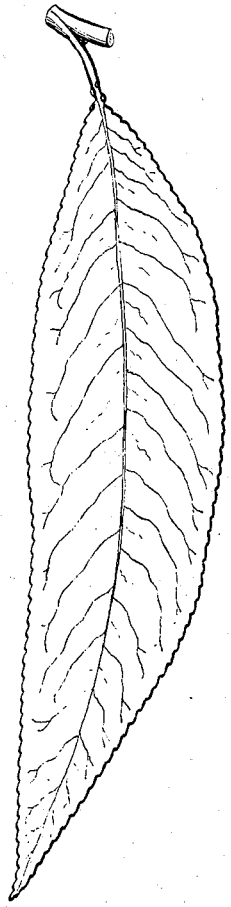
Figure 3 is an elevation of one of the leaves.
Figure 2:
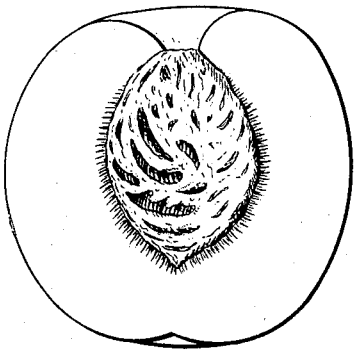
Figure 2 is a sectional view taken axially of the fruit and with the stone exposed.

The following is a detailed description of the nectarine tree and its fruit:

*Tree.*—The tree is of large size, vigorous, spreading, open, vase-formed, productive, and a regular bearer. The trunk of the tree is of medium size and has a medium bark. The branches of the tree, which are a brownish-green color, likewise are of medium size and have a medium bark. The lenticels are medium in number and size.

*Leaves.*—The leaves average 6 inches in length and 1½ inches in width, being smooth and of medium size and thickness. The leaves are a medium green color. The margin is crenate; the petiole of medium length and thickness; and the glands average four or more in number, being alternate, medium sized, reniform, and yellowish in color. The glands are usually located two on the petiole and two to four on the margin.

*Flowers.*—The flower buds are of medium size and length, plump and free. The flowers are pink, large and showy; blooming at approximately the same time as the Elberta peach.

*Fruit.*—The fruit is somewhat variable but extremely large in size, having an average axial diameter of 3 inches, and an average diameter transversely in the suture plane of 3 inches. The fruit is uniform, symmetrical, globose to oblong, and the suture is shallow with a marked depression beyond the pistil point. The ventral surface is rounded strongly and the lips are equal. The cavity is rounded and the suture shows on one side thereof, the cavity being approximately ⅜ inch in diameter and ¾ inch in breadth, and is usually marked with red lines. The base is rounded, while the apex is depressed and the pistil point is almost lacking.

The skin of the fruit is medium in thickness and toughness, and is tenacious to the flesh; there being a slight tendency to crack. The color of the skin is yellow, but is usually almost completely overspread with attractive red color. Down is wanting.

The flesh of the fruit is yellow, being somewhat streaked with red next to the stone. The surface of the pit cavity is red with yellow fibers. Amygdalin is moderate; juice and fibers are abundant; and the texture of the flesh is very firm. The flesh of the fruit ripens evenly and its flavor is acid and delicate; the aroma being distinct. The eating quality of the fruit is excellent, and the fruit is particularly well suited for table or dessert use.

The dates of first and last picking are approximately July 15 and August 5 respectively.

The stone of the fruit is a fully adherent cling with long fibers; the size of the stone being large, averaging 1⅜ inches in length, 1¼ inches in breadth and ⅝ inch in thickness. The stone is oval and full; the base oblique; the hilum broad and oval; the apex rounded; and the sides equal. The surface of the stone is irregularly furrowed and pitted throughout; the ridges are rounded and the pit angular. The ventral edge is thick and the dorsal edge is full with deep grooves throughout; the ridges being continuous. The stone is of a reddish color and has a slight tendency to split.

The variety has medium resistance to insects and plant disease, and these characteristics were determined in the following manner: The present variety was grown and fruited with several thousand other nectarine seedlings without spraying during the period in the nursery, and during such period said variety suffered from leaf curl, shot hole fungus, and brown rot to a certain extent, but considerably less than the average nectarine seedling of other varieties. Since removal from the nursery, the variety has been growing in my orchard, and the Bordeaux spray in the fall, followed by lime-sulphur plus lead arsenate at the red bud stage have satisfactorily controlled these diseases, as well as peach twig borer. In my orchards I have all the varieties grown to a commercial extent in California, viz: John Rivers, Gower, Quetta, Stanwick and Victoria. From my observations—which have been quite extensive—the claimed variety, in the orchard, is less susceptible than any of those identified above to delayed dormancy; it is less susceptible than John Rivers, Quetta and Stanwick to brown rot, but more susceptible thereto than Gower or Victoria; it is about as susceptible to leaf curl as Quetta and Stanwick, but more so than Gower and John Rivers; all varieties seem about equally susceptible to peach blight and peach twig borer; it is less susceptible to mildew than Gower, which has eglandular leaves; it is about as susceptible to mildew as other varieties, which all have leaves with reniform glands; and it is less marked by thrips injury than Quetta, Stanwick or John Rivers but more than Gower or Victoria. From the above observations I conclude that the present variety is of medium or average resistance to insects and disease.

The excellent eating and shipping qualities of the fruit of the present variety were recognized by me upon personal observation and comparison with other varieties, as well as by similar observation and comparison by other qualified persons, such as fruit packers and shippers to whom I have exhibited fruit of the variety; such characteristics being evidenced by the tasty and delicate flavor of the flesh of the fruit, as well as by its firmness, and which firmness—when the fruit is ripe—makes possible shipping thereof with a minimum of bruising or damage. Its shipping qualities are also enhanced by the fact that the fruit does not develop the undesirable softness toward the apex as does the Quetta variety.

As compared to the Quetta nectarine, which has previously been one of the largest commercial varieties, the present variety averages more than twenty-five per cent larger, has yellow instead of white flesh, and—of greater importance—is much firmer, keeps and ships better, and is of better eating quality. As compared to the Humboldt, Lippiatt, and Hunter varieties—which are all relatively small, soft, freestone varieties, the claimed variety is a very large, firm, clingstone nectarine. The Humboldt and Lippiatt varieties have not been commercially successful in the State of California, due to their small size, low productiveness, delayed dormancy and susceptibility to shot hole fungus, brown rot and mildew. The Hunter variety has not been brought into California on a commercial scale, although I have observed this variety, and apparently it has the same difficulties as enumerated above.

The tree and its fruit above described may vary in slight details due to climatic and soil conditions under which the variety may be grown.

Having thus described my invention I claim:

The new and distinct variety of nectarine, as herein disclosed, characterized by yellow and firm-fleshed cling-stone fruit of large size, superior eating quality, and excellent shipping quality; all as compared to the Quetta nectarine.

FREDERIC W. ANDERSON.